(12) United States Patent
Frieze et al.

(10) Patent No.: US 6,230,888 B1
(45) Date of Patent: May 15, 2001

(54) INSTRUMENT COUNT STAND

(76) Inventors: Marcia A. Frieze, 45 Berkery Pl., Alpine, NJ (US) 07620-0672; Ron Amster, 169 E. 91st St., #10A, New York, NY (US) 10128

( * ) Notice: Subject to any disclaimer, the term of this patent is extended or adjusted under 35 U.S.C. 154(b) by 0 days.

(21) Appl. No.: 09/600,391

(22) PCT Filed: Jan. 14, 1998

(86) PCT No.: PCT/US98/00731

§ 371 Date: Jul. 14, 2000

§ 102(e) Date: Jul. 14, 2000

(87) PCT Pub. No.: WO99/36106

PCT Pub. Date: Jul. 22, 1999

(51) Int. Cl.[7] .................................................. B65D 83/10

(52) U.S. Cl. .................. 206/370; 206/372; 206/560; 211/70.6; 422/300; 422/310

(58) Field of Search ................................. 206/370, 372, 206/373, 369, 363, 438, 560, 561, 565; 211/70.6; 422/104, 297, 300, 310

(56) References Cited

U.S. PATENT DOCUMENTS

| | | |
|---|---|---|
| 3,564,662 | 2/1971 | Dold . |
| 3,925,014 | 12/1975 | Langdon . |
| 4,229,420 | 10/1980 | Smith et al. . |
| 4,342,391 | 8/1982 | Schainholz . |
| 4,541,992 | 9/1985 | Jerge et al. . |
| 4,577,755 | 3/1986 | Ramsay . |
| 4,643,303 | 2/1987 | Arp et al. . |
| 4,865,821 | 9/1989 | Langdon . |
| 4,943,939 | 7/1990 | Hoover . |
| 5,137,151 | 8/1992 | Choate . |
| 5,284,632 | 2/1994 | Kudla et al. . |
| 5,433,929 | 7/1995 | Rhihima et al. . |
| 5,449,069 | 9/1995 | Pijanowski et al. . |
| 5,451,380 | 9/1995 | Zinnanti . |

*Primary Examiner*—Luan K. Bui
(74) *Attorney, Agent, or Firm*—Woodbridge & Associates, P.C.; Richard C. Woodbridge (57) ABSTRACT

The disclosure relates to an instrument count stand for supporting scissors or scissor-like instruments having a pair of blades and a pair of handles. The stand includes a base having a plurality of slots for receiving portions of the instruments. A pair of side walls extending from the base support a roller. A handle is attached to the roller for moving the roller from a first position disengaged from the handles of the instruments to a second position which contacts the handles of the instruments and spreads the handles and accordingly the blade-like members of the instruments.

19 Claims, 7 Drawing Sheets

INSTRUMENT COUNT STAND

BACKGROUND OF THE INVENTION

1. Field of the Invention

The invention generally comprises a surgical instrument count stand for holding, counting, and sterilizing surgical scissors and other ring handle instruments.

2. Description of Related Art

When performing surgical procedures, it is highly desirable to be able to organize, count, and support surgical instruments, such as scissors, needle holders and clamps, prior to and after sterilization. It is also desirable to spread the blades of the scissors prior to sterilization so that the entire surface of the scissors is appropriately cleaned and sterilized. The prior art literature discloses a number of devices to hold surgical scissors for that purpose.

One of the most common prior art devices is referred to as a "stringer". It gets its name from the fact that a rod, or similar mechanism, passes through one of the handles of the surgical scissors as they sit on a rack. Movement of the rod causes the handles of the scissors to move apart thereby spreading the blades for sterilization. Examples of prior art stringer instrument racks can be found in U.S. Pat. Nos.: 3,925,014; 5,137,151; and 5,449,069.

Another category of prior art instrument count racks, or stands, employ a bar which, unlike the stringers, does not pass through one of the handles of the scissors but, instead, pushes the handles away from each other. Examples of such prior art devices can be found in U.S. Pat. Nos.: 4,342,391; 4,577,755; and 4,865,821.

A variation on the foregoing is a movable wedge or bracket mechanism that cams the scissors apart using an inclined plane or similar surface. Such a device is described, for example in U.S. Pat. No. 4,229,420.

More recently, computerized devices have been employed to count and sterilize instruments. They are, however, relatively complex and expensive. Note, for example, the surgical count stand described in U.S. Pat. No. 4,943,939.

Lastly, there are a variety of passive instrument count stands that hold the instruments in position but do not necessarily assist in spreading the blades. Examples of the foregoing are found in U.S. Pat. Nos. 3,564,662; 4,541,992; 4,643,303; 5,284,632; 5,451,380; and 5,433,929.

One of the major difficulties with prior art instrument count stands is that surgical scissors come in a wide variety of shapes and sizes. A stand that might be appropriate for one size scissors may be totally inappropriate for another size. Also, many prior art instrument count stands require several steps, or procedures, in order to spread the scissors. For example, prior art "stringer" instrument stands require that each of the individual handles be strung over a rod. Insofar as understood, none of the prior art appears to hint, teach or suggest an instrument count stand that will adequately work with a wide variety of different scissors sizes and in which the steps of holding, spreading and locking can be essentially done in one simple movement of a handle. It was in the context of the foregoing prior art that the present invention arose.

SUMMARY OF THE INVENTION

Briefly described, the invention comprises an instrument count stand or sterilization rack that holds between 16 and 42 scissors of various sizes. The stand includes an aluminum base with horizontal slots which serve to hold the scissors' handles, a bracket that serves as a stop for small instruments, two sidewalls including a slot for engaging an axle, a vertical slot rack; two leaf spring handle locking clips, a roller for spreading the scissors handles, and a wire handle connected to the roller. Between 16 and 42 scissors, of various sizes, are arranged on the count stand in the vertical slots with their handles placed in the horizontal slots. The stand comes in three sizes: a small size 10, such as shown in FIGS. 1–3C that holds 16 scissors; a medium size that holds 29 scissors; and, a large size that holds 42 scissors. The roller is preferably formed from an aluminum perforated tube with end plug which roll on a wire axle. The wire axle is retained within the slots on the two opposing sidewalls. Pulling the wire handle forward or backward moves the roller forward or backward as the axle translates in the axle slots in the sidewalls. As the roller is brought forward, under the influence of the handle, the roller is "squeezed" in between the scissors handles (sometimes referred to as "loops" or "rings") forcing them open and, consequently, spreading the blades apart. The forward motion of the roller which spreads the blades apart, also serves as a lock preventing the scissors handles from moving out of the horizontal slots. After the roller has been pushed or pulled all the way forward, the handle is rotated and locked in position by the pair of respective leaf springs. The stand and scissors are then ready for sterilization. In one action, the spreading mechanism spreads the blades, locks and secures the instruments to the count stand, and prepares them for sterilization. After sterilization, as the handle is unlocked and the roller is pushed backward, the instruments are also unlocked and ready for use.

These and other features of the invention will be more fully understood by reference to the following drawings.

DETAILED DESCRIPTION OF THE PREFERRED EMBODIMENT

During the course of this description like numbers will be used to identify like elements according to the different figures that illustrate the invention.

Figure 1A:
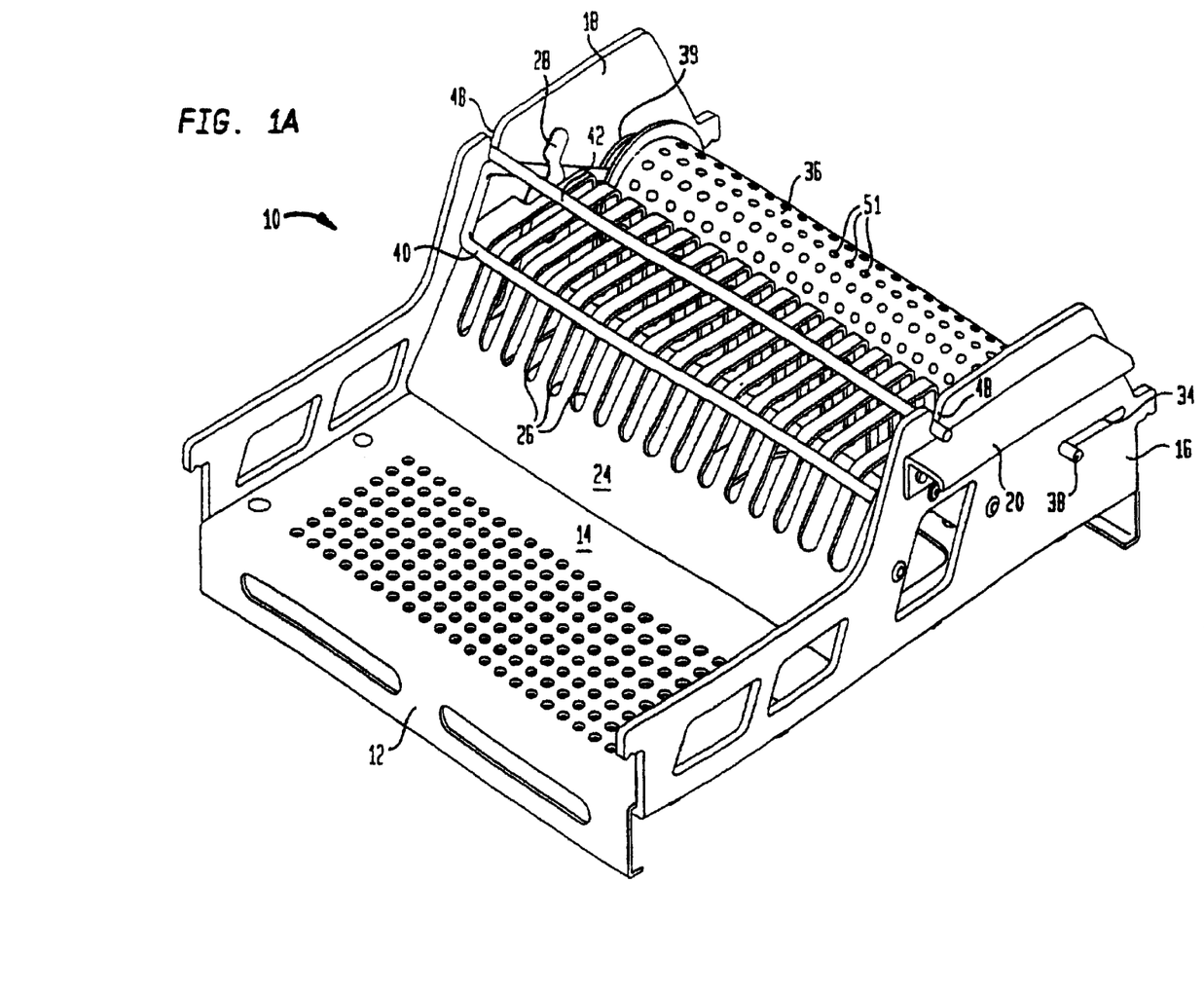
FIG. 1A is a front perspective view of the preferred embodiment of the instrument count stand.
Figure 1B:
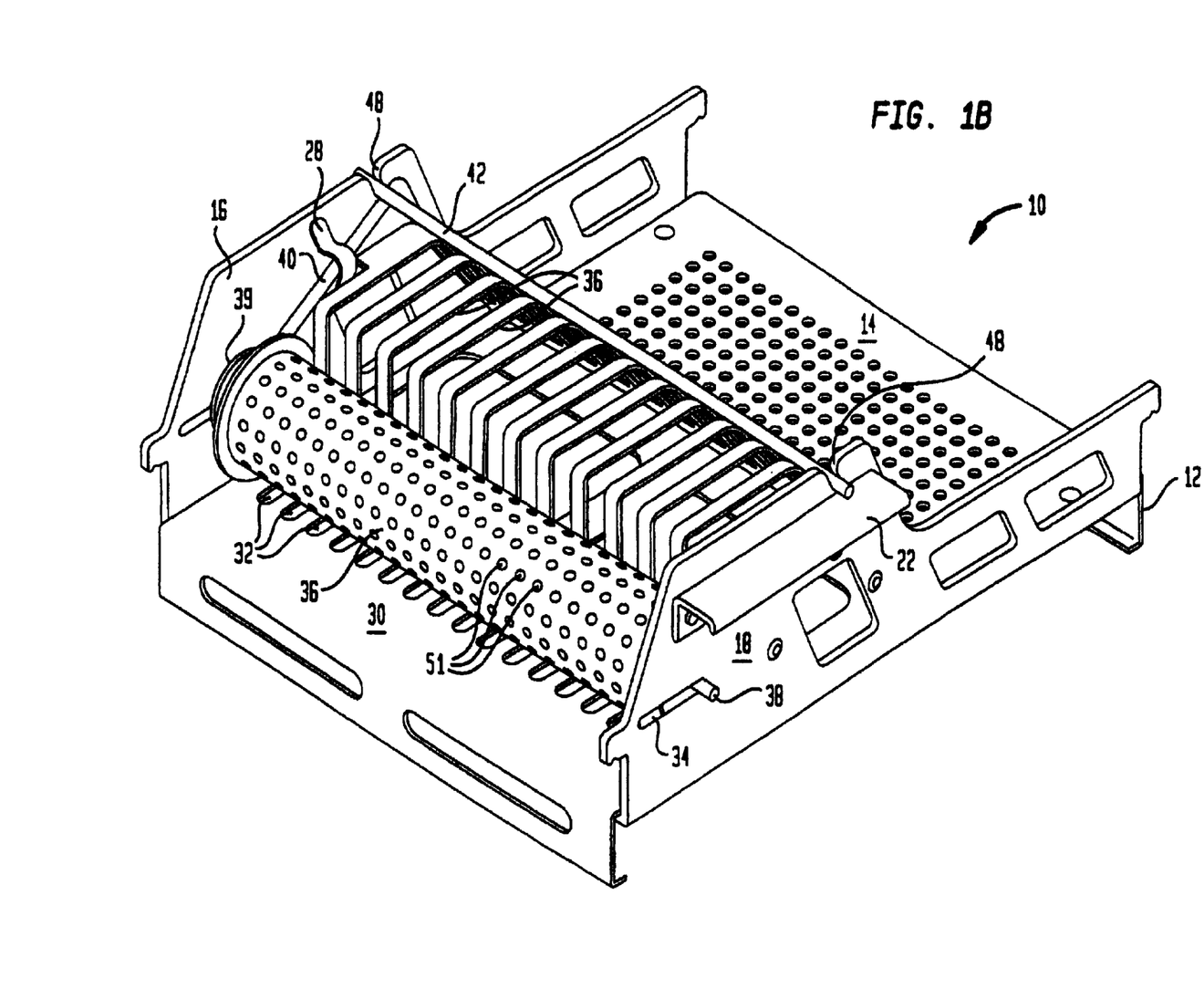
FIG. 1B is a rear perspective view of the instrument count stand of FIG. 1A.
Figure 2A:
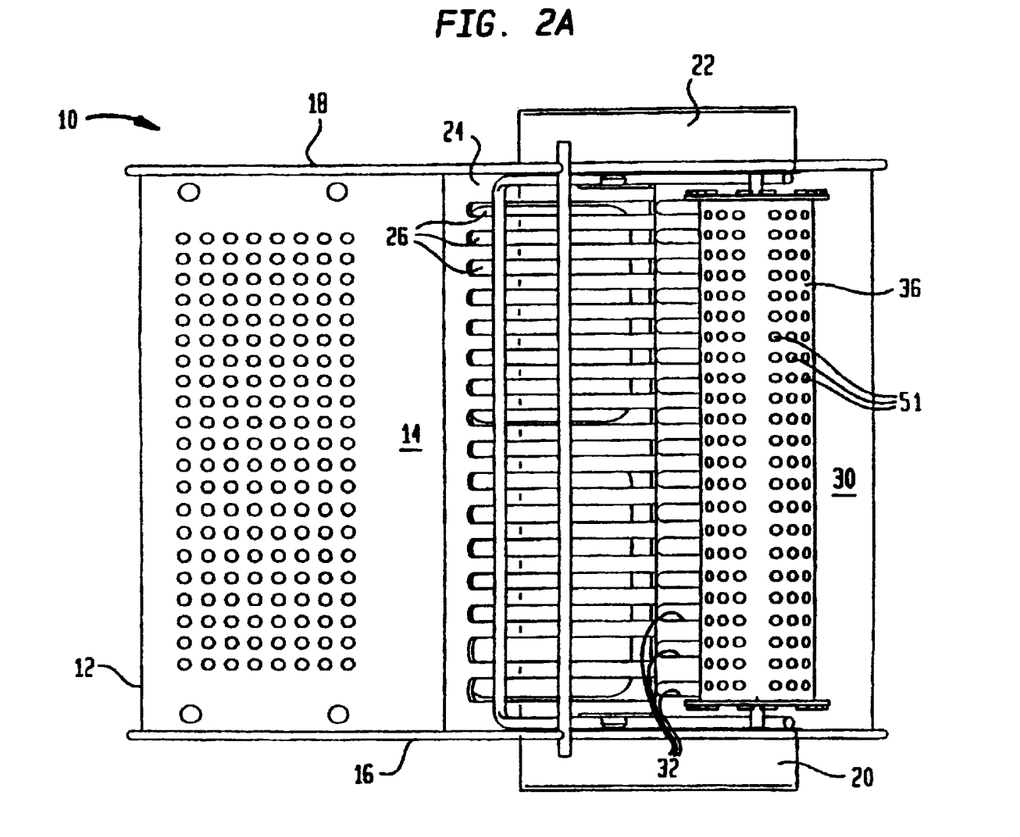
FIG. 2A is a top plan view of the instrument count stand in the locked position.
Figure 2B:
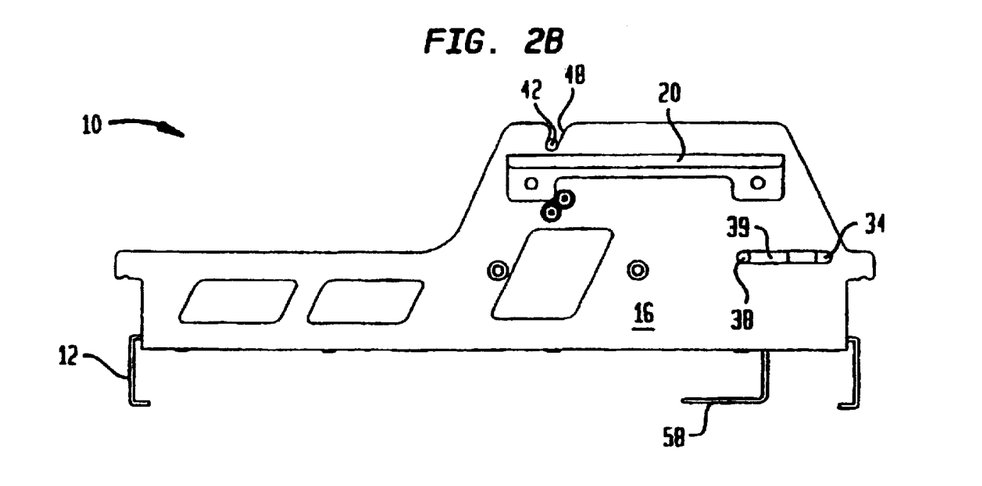
FIG. 2B is a left side elevational view of the instrument count stand in the locked position.
Figure 2C:
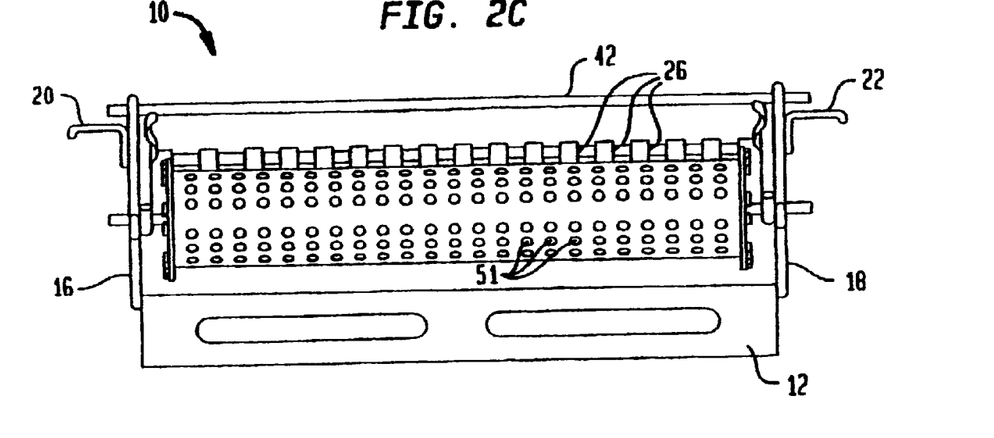
FIG. 2C is a rear elevational view of the instrument count stand in the locked position.
Figure 2D:
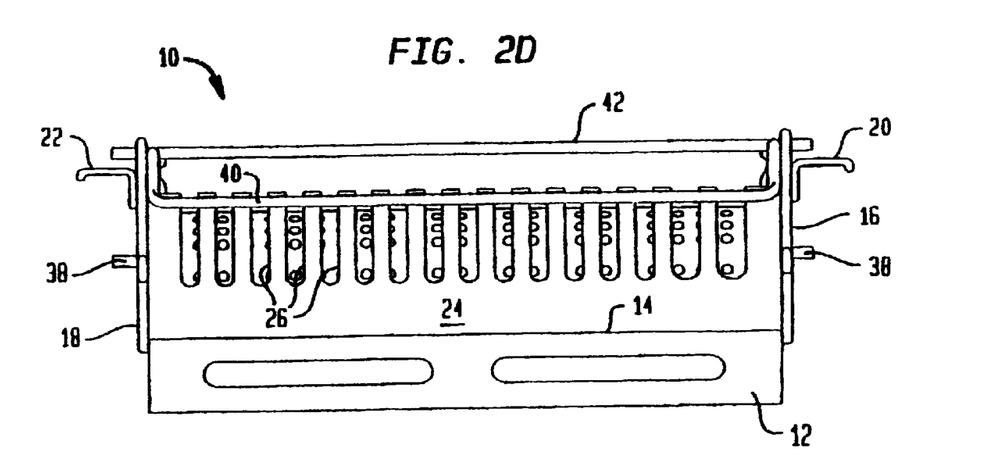
FIG. 2D is a front elevational view of the instrument count stand in the locked position.

The preferred embodiment of the invention 10 is illustrated in a front perspective shown in FIG. 1A and a rear perspective shown in FIG. 1B. FIGS. 2A, 2B, 2C and 2D illustrate top plan views, left side elevational views, rear elevational views, and front elevational views, respectively.

The preferred embodiment 10 includes a base 12 having a front floor section 14. A left sidewall 16 and a right sidewall 18 are located on opposite sides of base 12 and are attached thereto. A left sidewall handle 20 is attaches to the left sidewall 16. Similarly, a right sidewall handle 22 is attached to the right sidewall 18. Handles 20 and 22 are employed to lift the count stand 10 and transport it to a sterilization station and back.

A vertical slotted scissors holder section 24 rests on base 12 and spans the distance between left and right sidewalls 16 and 18, respectively. A plurality of slots 26 is intended to support between 16 and 42 scissors 52, respectively. Each pair of scissors 52 includes a pair of blades 54 and a pair of handles or loops 56. Scissors 52 normally comprise surgical scissors of varying sizes and shapes. According to the preferred embodiment of the invention 10, the vertical scissors holder section 24 includes 16 slots 26, but the number of slots 26 could be greater or lesser depending upon the needs of the user. The stand comes in three sizes, as previously discussed: a small size 10, such as shown in FIGS. 1–3C, which holds 16 scissors; a medium size that holds 29 scissors; and, a large size that holds 42 scissors.

Base 12 also includes a rear section, or deck, 30. A plurality of horizontal scissors handle slots 32 are located in the rear deck 30 of the base 12. Horizontal slots 32 receive one of the two handles, or loops, 56 of scissors 52. In addition, in order to prevent small scissors 52, or instruments, from falling through the horizontal slots 32, a small instrument stop bracket 58 is attached to the bottom of base 12. See FIG. 2B.

A roller 36, preferably formed from a perforated aluminum or stainless steel tube, is located above the rear deck 30 of base 12. A pair of roller axle caps, or plugs, 39 are located at opposite ends of roller 36. A roller axle wire 38, supported by axle caps 39, passes through the length of roller 36 and is received in slot 34 located in each of the sidewalls 16 and 18, respectively. In order to securely lock small and large instruments, including scissors, clamps and needle holders, the position of axle slots 34, in terms of height and distance from the back side of the holder 24, and the diameter of roller can be important. Slot 34 preferably has a length of 1 inch. The preferred diameter size of the roller 36 was found to be 1.5"±0.15" for this embodiment.

Figure 3A:
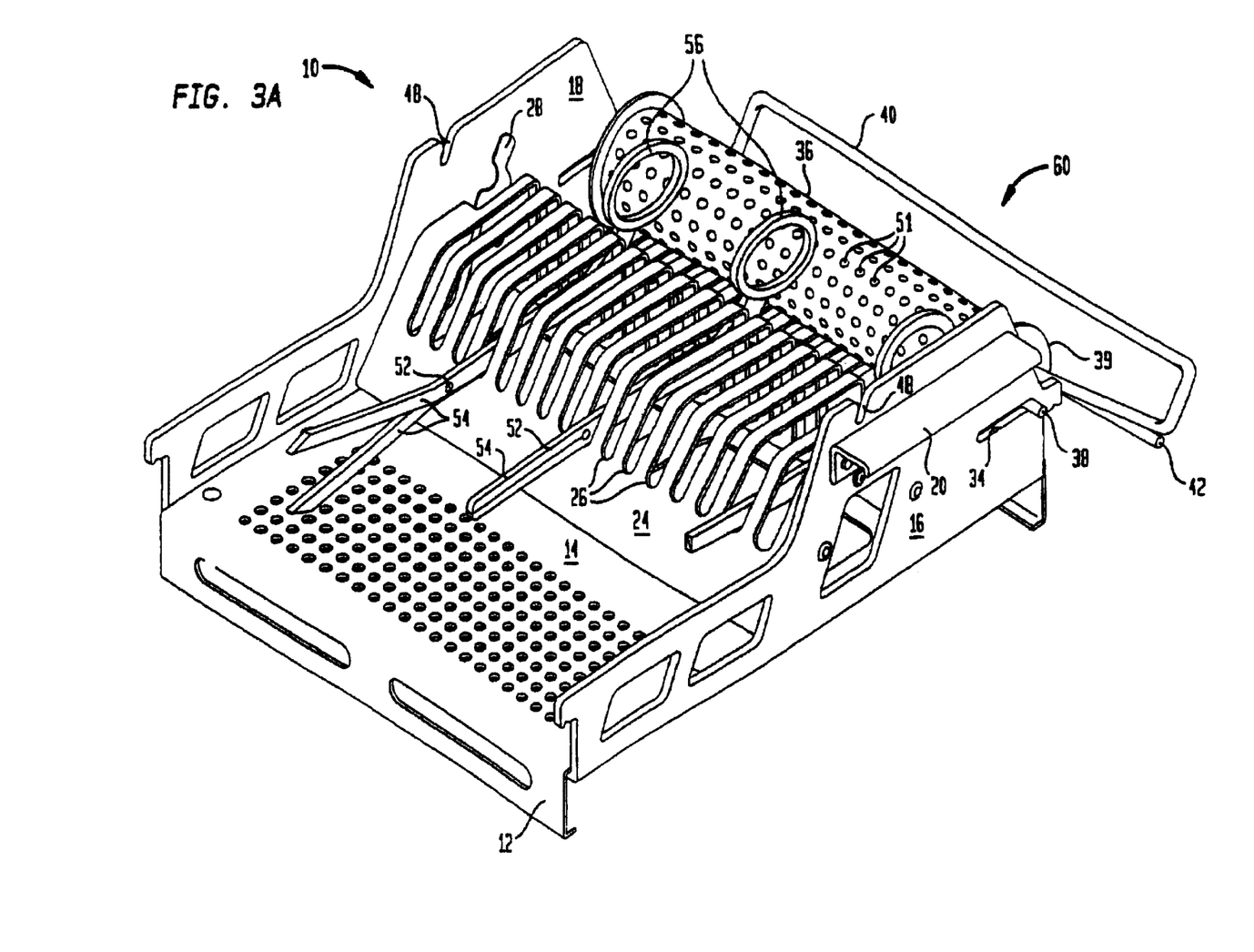
FIG. 3A is a detailed view of the instrument count stand in the first or unlocked position with the roller in the rear, disengaged position and the handle fully back.
Figure 3B:
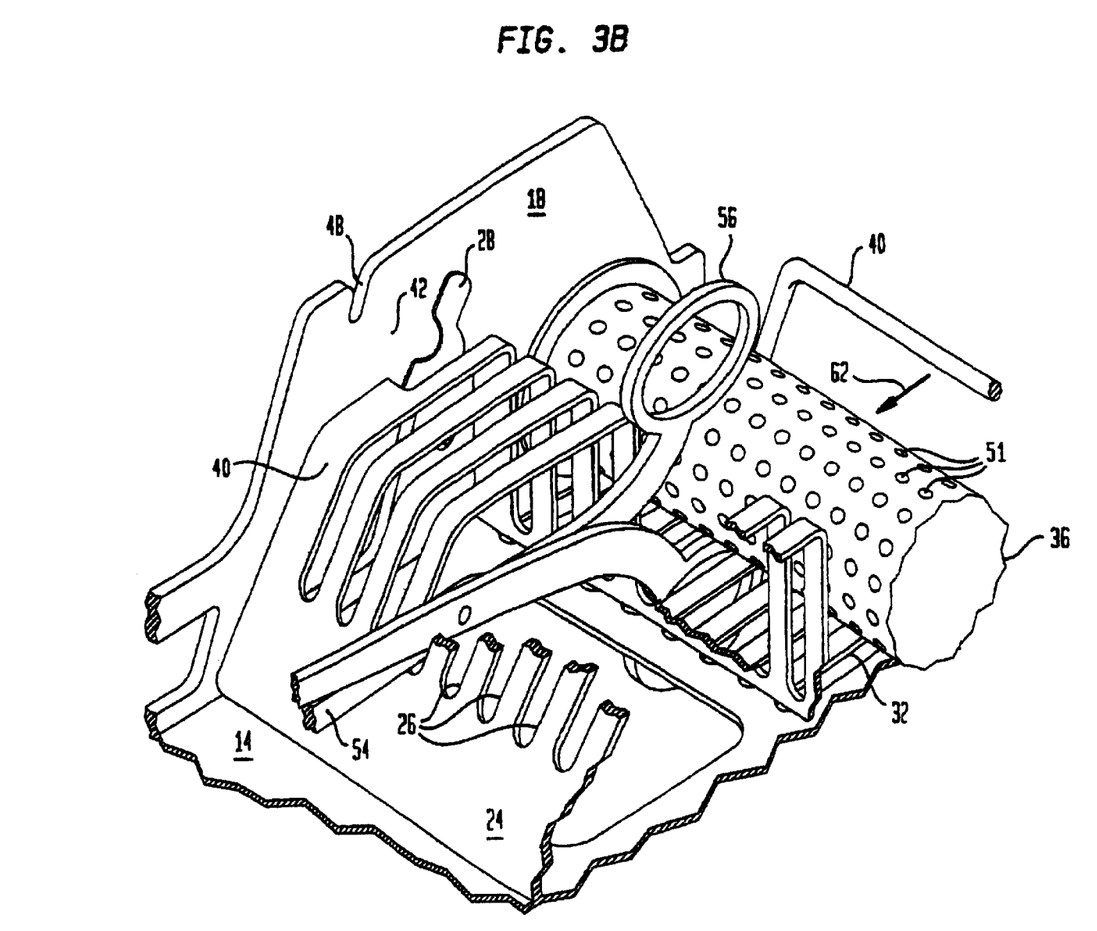
FIG. 3B is a detailed view of the instrument count stand in an intermediate position with the roller moving toward the fully forward position spreading the scissors handles but with the handles remaining back.
Figure 3C:
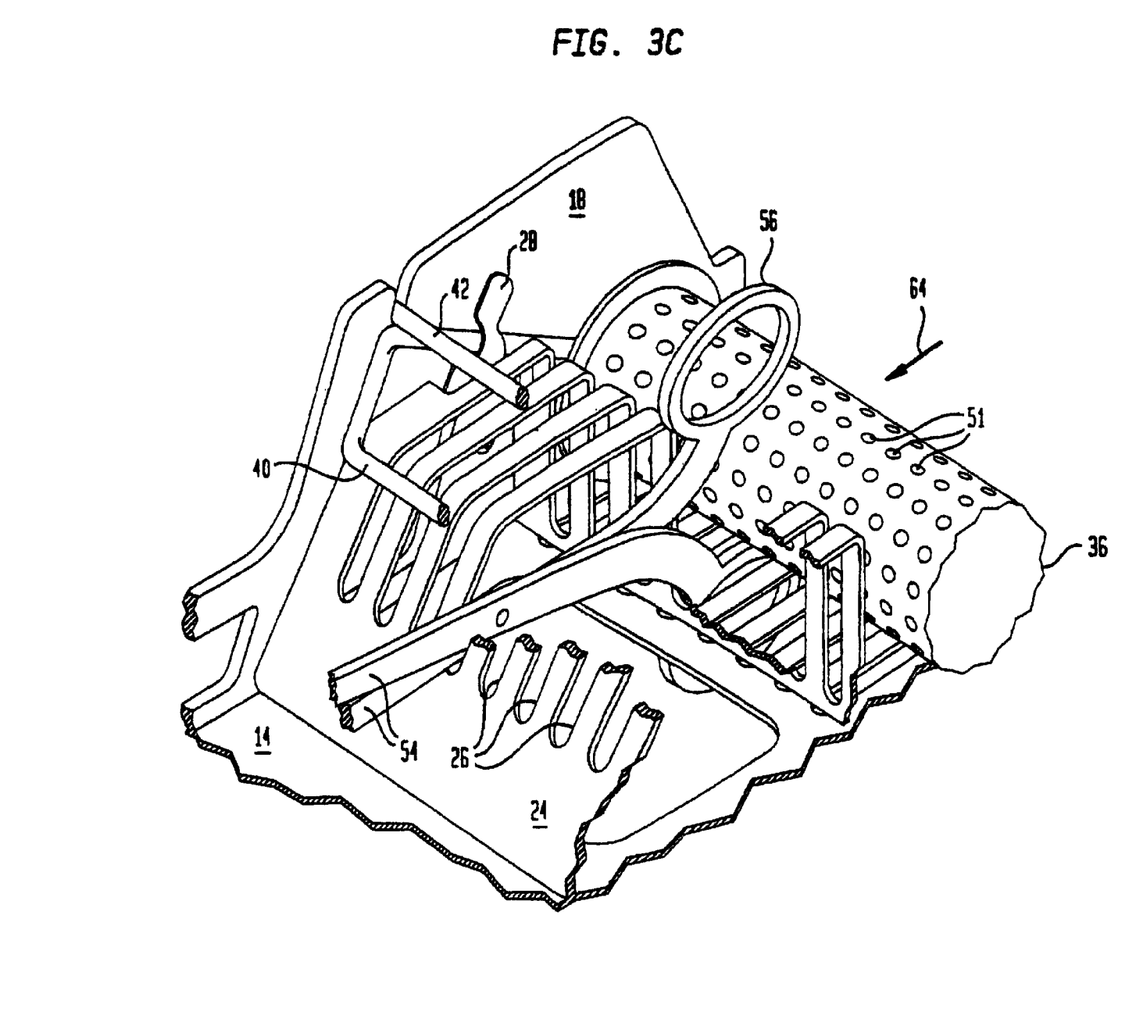
FIG. 3C is a detailed view of the instrument count stand with the roller and handle fully forward and the handles in the second or locked position.

A wire handle 40 is attached at opposite ends to the roller axle caps 39 and forms a bail with respect thereto. Wire handle 40 includes a stop bar section 42 the end portions of which are receivable in slots 48 on the top of sidewalls 16 and 18, respectively. When wire handle 40 is rotated for its first or fully rearward position 60, as illustrated in FIGS. 3A, to its second or fully forward position 64, as illustrated in FIG. 3C, the stop bar 42 is received in slots 48. In addition, the sidewalls 16 and 18 inlcude leaf spring locks 28 which engage the wire handle 40 in the full forward position 64 as shown in FIG. 3C.

As previously described, roller 36 comprises an aluminum tube with a plurality of perforations 51 therein. A plurality of longitudinal seams 50, usually four in number, extend from one end of the roller 36 to the other.

In operation, the invention 10 is employed in the following fashion.

First, the instrument count stand 10 is placed in the loading, or first, position 60 as illustrated in FIG. 3A. In the loading position, the wire handle 40 is rotated backwards and the roller 36 is in its most rearward position. The roller axle 38 is in the most rearward position in axle slots 34 in sidewalls 16 and 18. Between 1 and 16 scissors 52 can be placed on the count stand with the bodies of each of the scissors 52 received in the vertical slots 26 of the vertical section 24 and with one of the handles, or loops, 56 of the scissors 52 received in the horizontal slots 32 in the rear floor 30 of base 12. The scissors 52 are slightly inclined with the handles, or loops, 52 pointing downward in vertical slots 26 to allow for easier spreading of blades 54. The small instrument stop bracket 58 prevents small instruments, or scissors 52, from falling through the horizontal slots 32.

The wire handle 40 is either pushed or pulled forward in the direction of arrow 62 forcing the roller 36 to squeeze the scissors handles 56 apart as shown in FIG. 36. This intermediate position 62, also referred to as the spreading ode, causes the blades 54 of the scissors 52 to spread thereby exposing them to full sterilization. One of the major advantages of roller 36 is that is can rotate and cam, or squeeze, open scissors handles 56 of a very wide variety of sizes ranging from relatively small to relatively large. In contrast, many prior art in count stands only operate well with scissors in a narrow range of sizes.

Continued movement of the wire handle 40 brings it to the second, or fully locked, position 64 as illustrated in FIG. 3C. The handle 40 is positioned so that it limits the vertical movement of scissors' blades 54. In the second, locked position the wire handle 40 is rotated fully forward so that the spring locks 28 on opposite sidewalls 16 and 18 engage the wire handle 40 and lock it into position. Simultaneously, the stop bar 42 engages slots 48 in the top of sidwalls 16 and 18. In the second, or fully locked position 64, the instruments 52 are securely held in position and can be transported to a sterilization device, such as an autoclave. Conversely, the instruments 52 can be removed safely from an autoclave and transported to a location where they can be removed. Another advantage, as is apparent from reviewing positions 60, and 64 of FIGS. 3A and 3C, is that the operation can be performed in a single motion with one hand.

It will be clear from the foregoing that the present invention has several advantages over typical prior art instrument count stands. First, the invention 10 is relatively easy to operate and requires few operator actions. This is a major advantage in terms of saving time and is safer for the operator because it gives the operator fewer opportunities to nick or cut him or herself. Second, as compared to passive instrument count stands, the invention 10 consistently , and firmly, spreads the jaws or blades 54 of the scissors 52 apart for better sterilization. Third, the preferred embodiment 10 securely holds large instruments, such as scissors 52, as well as small instruments. In addition, small instruments 52 have the advantage of a stop bracket 58 located on the bottom of base 12 to prevent them from falling through horizontal slots 32. Fourth, the invention 10 has the advantage that an operator can remove any single instrument 52 from the rack 10 without having to clear or move other instruments 52 in order to reach them. In contrast, many prior art instrument count stands, such as the "stringer" variety, require that all of the instruments be manipulated before a single individual one can be removed. Fifth, the unique roller design permits the invention to be used with a very wide variety of scissors sizes without jamming or hesitation. Sixth, there are no separate parts. The invention 10 acts as a single, integrated unit with no parts to lose. Seventh, the instruments 52 can be locked in position with only one hand in a single motion. Eighth, the instruments 52 are well separated which not only protects them from each other but also makes them easier to count, easier to select and easier to sterilize.

While the invention has been described with reference to the preferred embodiment thereof, it will be appreciated by those of ordinary skill in the art that modifications can be made to the structure and method of the present invention without departing from the spirit and scope thereof.

What is claimed is:

1. An instrument count stand apparatus (10) for supporting scissors (52) each having a pair of blades (54) and a pair of handles (56), said apparatus comprising:

a base (12) having a plurality of slots (26, 32) therein for receiving said scissors (52);

a pair of sidewalls (16, 18) attached to said base (12);

a roller (36) supported by said sidewalls (16, 18); and handle means (40) attached to said roller (36) for moving said roller (36) from a first position (60) disengaged from said pair of handles (56) of said scissors (52) to a second position (64) which contacts both of said handles (56) and spreads the handles (56) and blades (54) of said scissors (52).

2. The apparatus of claim 1 wherein said sidewalls (16, 18) further include a pair of slots (34) therein and said roller (36) includes an axle (38) which extends beyond said roller and into said pair of slots (34) respectively, wherein said axle (38) moves along said slots (34) when said handle means (40) moves from said first disengaged position (60) to said second position (64).

3. The apparatus of claim 2 wherein said base (12) further includes a vertical central section (24) for supporting said scissors (52).

4. The apparatus of claim 3 wherein said slots in said base (12) comprise vertical slots (26) in said vertical section (24) for supporting said scissors (52) and horizontal slots (32) in said base (12) for supporting the handles (56) of said scissors (52).

5. The apparatus of claim 4 wherein said base (12) further comprises:

a small instrument stop bracket (58) for preventing small scissors (52) from falling through said horizontal slots (32).

6. The apparatus of claim 5 wherein said roller (36) has a diameter in the range of 0.85 to 1.15 inches.

7. The apparatus of claim 6 wherein said roller (36) has perforations (51) therein.

8. The apparatus of claim 7 further comprising:

a locking means for locking said handle means (40) in the second position (64), said locking means comprising a pair of leaf springs (28) for engaging said handle means (40).

9. The apparatus of claim 8 further comprising:

a stop bar (42) located on the top of said handle means (40); and, a pair of slots (48) in the top of said sidewalls (16, 18) for receiving said stop at (42) when said handle means (40) and roller (36) are in the second position 64.

10. An instrument count stand apparatus (10) for supporting scissors (52) each having a pair of blades (54) and a pair of handles (56), said apparatus comprising:

a base (12) having a plurality of slots (26, 32) therein for receiving said scissors (52);

a pair of sidewalls (16, 18) attached to said base (12), said sidewalls (16, 18) further including a pair of slots (34) therein;

a roller (36) supported by said sidewalls (16, 18), said roller (36) including an axle (38) which extends beyond said roller (36) and into said pair of slots (34) respectively, handle means (40) attached to said roller (36) for moving said roller (36) from a first position (60) disengaged from said scissors (52) to a second locked position (64) which spreads the handles (56) and blades (54) of said scissors (52), wherein said axle (38) moves along said slots (34) when said handle means (40) moves from said first disengaged position (60) to said second locked position (64).

11. An instrument count stand apparatus (10) for supporting scissor instruments (52) each having a pair of extending portions (54) and a pair of handles (56), said apparatus comprising:

a base (12) having a plurality of slots (26, 32) therein for receiving said instruments (52);

a pair of sidewalls (16, 18) attached to said base (12);

a roller (36) supported by said sidewall (16, 18); and, handle means (40) attached to said roller (36) for moving said roller (36) from a first open position (60) disengaged from said pair of handles (56) of said instruments (52) to a second locked position (64) which contacts both of said handles (56) and spreads the handles (56) and extending portions (54) of said instruments (52).

12. The apparatus of claim 11 wherein said sidewalls (16, 18) further include a pair of slots (34) therein and said roller (36) includes an axle (38) which extends beyond said roller and into said pair of slots (34) respectively, wherein said axle (38) moves along said slots (34) when said handle means (40) moves from said first open position (60) to said second locked position (64).

13. The apparatus of claim 11 wherein said base means (12) further includes a vertical central section (24) for supporting said instruments (52).

14. The apparatus of claim 13 wherein said slots in said base (12) comprise vertical slots (26) in said vertical section (24) for supporting said instruments (52) and horizontal slots (32) in said base (12) for supporting the handles (56) of said instruments (52).

15. The apparatus of claim 14 wherein said base (12) further comprises:

a small instrument stop bracket (58) for preventing small instruments (52) from falling through slots (32).

16. The apparatus of claim 11 wherein said roller (36) has a diameter in the range of 0.85 to 1.15 inches.

17. The apparatus of claim 11 wherein said roller (36) has perforations (51) therein.

18. The apparatus of claim 11 further comprising:

a locking means for locking said handle means (40) in the fully locked position, said locking means comprising a pair of leaf springs (28) for engaging said handle means (40).

19. The apparatus of claim 11 further comprising:

a stop bar (42) located on the top of said handle means (40); and, a pair of (48) in the top of said sidewalls (16, 18) for receiving said stop bar (42) when said handle means (40) and roller (36) are in the second locked position.

* * * * *